(12) United States Patent
Jackson (10) Patent No.: US 8,927,521 B2
(45) Date of Patent: Jan. 6, 2015

(54) CYCLIC ADENOSINE MONOPHOSPHATES FOR REDUCING THE FORMATION OF ADHESIONS

(75) Inventor: Edwin Kerry Jackson, Pittsburgh, PA (US)

(73) Assignee: University of Pittsburgh—of the Commonwealth System of Higher Education, Pittsburgh, PA (US)

( * ) Notice: Subject to any disclaimer, the term of this patent is extended or adjusted under 35 U.S.C. 154(b) by 745 days.

(21) Appl. No.: 13/128,175

(22) PCT Filed: Nov. 5, 2009

(86) PCT No.: PCT/US2009/063386
§ 371 (c)(1),
(2), (4) Date: Aug. 25, 2011

(87) PCT Pub. No.: WO2010/054068
PCT Pub. Date: May 14, 2010

(65) Prior Publication Data
US 2011/0301111 A1   Dec. 8, 2011

Related U.S. Application Data

(60) Provisional application No. 61/113,068, filed on Nov. 10, 2008.

(51) Int. Cl.
| | | |
|---|---|---|
| *A61K 31/70* | (2006.01) | |
| *A01N 43/04* | (2006.01) | |
| *A61K 31/122* | (2006.01) | |
| *A61K 31/16* | (2006.01) | |
| *A61K 31/185* | (2006.01) | |
| *A61K 31/194* | (2006.01) | |
| *A61K 31/444* | (2006.01) | |

(52) U.S. Cl.
CPC .............. *A61K 31/122* (2013.01); *A61K 31/16* (2013.01); *A61K 31/185* (2013.01); *A61K 31/194* (2013.01); *A61K 31/444* (2013.01)
USPC ......................................... 514/47; 536/26.13

(58) Field of Classification Search
CPC ..... A61K 31/22; A61K 31/16; A61K 31/444; A61K 31/194; A61K 31/185
See application file for complete search history.

(56) References Cited

U.S. PATENT DOCUMENTS

| 4,211,770 A | 7/1980 | Voorhees |
| 5,599,798 A | 2/1997 | Takasugi et al. |
| 6,566,371 B2 | 5/2003 | Jackson |

OTHER PUBLICATIONS

Al-Chalabi et al., Value of a Single Intraperitoneal Dose of Heparin in Prevention of Adhesion Formation: An Experimental Evaluation in Rats, Int. J. Fertil., 1987, pp. 332-335, vol. 32, No. 4.
Azziz et al., Microsurgery Alone or with INTERCEED Absorbable Adhesion Barrier for Pelvic Sidewall Adhesion Re-Formation, Surgery, Gynecology & Obstetrics, Aug. 1993, pp. 135-139, vol. 177.
Balyasnikova et al., Cyclic Adenosine Monophosphate Regulates the Expression of the Intercellular Adhesion Molecule and the Inducible Nitric Oxide Synthase in Brain Endothelial Cells, Journal of Cerebral Blood Flow and Metabolism, 2000, pp. 688-699, vol. 20.
Bateman et al., Prevention of postoperative peritoneal adhesions with ibuprofen, Fertility and Sterility, Jul. 1982, pp. 107-108, vol. 38, No. 1.
Caballero et al., Effects of Ringer's Lactate and Fibrin Glue on Postsurgical Adhesions, Journal of Reproductive Medicine, Feb. 1992, pp. 141-143, vol. 37, No. 2.
Daly et al., Adenosine Receptors: Selective Agonists and Antagonists, Molecular Biology to Integrated Physiology, 1995, pp. 157-166, Chapter 19, Kluwer Academic Publishers, Boston.
Diamond et al., Reduction of adhesions after uterine myomectomy by Seprafilm membrane (HAL-F): a blinded, prospective, randomized, multicenter clinical study, Fertility and Sterility, Dec. 1996, pp. 904-910, vol. 66, No. 6.
Diamond et al., Reduction of de novo postsurgical adhesions by intraoperative precoating with Sepracoat (Hal-C) solution: a prospective, randomized, blinded, placebo-controlled multicenter study, Fertility and Sterility, Jun. 1998, pp. 1067-1074, vol. 69, No. 6.
Dizerega et al., A randomized, controlled pilot study of the safety and efficacy of 4% icodextrin solution in the reduction of adhesions following laparoscopic gynaecological surgery, Human Reproduction, 2002, pp. 1031-1038, vol. 17, No. 4.
Farquhar et al., Barrier agents for preventing adhesions after surgery for subfertility (Review), Cochrane Database of Systematic Reviews, 1999, 40 pages, Issue 2.
Fazio et al., Reduction in Adhesive Small-Bowel Obstruction by Seprafilm Adhesion Barrier After Intestinal Resection, Diseases of the Colon and Rectum, 2005, pp. 1-11, vol. 49.
Franklin et al., Reduction of Ovarian Adhesions by the Use of Interceed, Obstetrics & Gynecology, Sep. 1995, pp. 335-340, vol. 86, No. 3.
Haney et al., Expanded polytetrafluoroethylene (Gore-Tex Surgical Membrane) is superior to oxidized regenerated cellulose (Interceed TC7) in preventing adhesions, Fertility and Sterility, May 1995, pp. 1021-1026, vol. 63, No. 5.
Helfman et al., A Homogeneous Cyclic CMP Phosphodiesterase Hydrolyzes Both Pyrimidine and Purine Cyclic 2':3'- and 3':5'-Nucleotides, The Journal of Biological Chemistry, Jan. 25, 1982, pp. 1044-1047, vol. 257, No. 2.
Helfman et al., Purification to Homogeneity and General Properties of a Novel Phosphodiesterase Hydrolyzing Cyclic CMP and Cyclic AMP, The Journal of Biological Chemistry, Jun. 25, 1981, pp. 6327-6334, vol. 256, No. 12.
Hunsucker et al., The 5'-nucleotidases as regulators of nucleotide and drug metabolism, Pharmacology & Therapeutics, 2005, pp. 1-30, vol. 107.
Interceed (TC7) Adhesion Barrier Study Group, Prevention of postsurgical adhesions by Interceed (TC7), an absorbable adhesion barrier: a prospective, randomized multicenter clinical study, Fertility and Sterility, Jun. 1989, pp. 933-938, vol. 51, No. 6.

(Continued)

*Primary Examiner* — Lawrence E Crane
(74) *Attorney, Agent, or Firm* — The Webb Law Firm (57) ABSTRACT

Provided herein are methods of reducing adhesion formation in a subject, for example, post-surgical abdominal and pelvic adhesions. The methods include the step of administering to the subject in need thereof a compound chosen from 2',3'-cyclic adenosine monophosphate, analogs thereof, and pharmaceutically acceptable salts thereof, able to reduce the formation of adhesions in a subject as compared to adenosine monophosphate, in an amount effective to reduce adhesions.

11 Claims, 3 Drawing Sheets

(56) References Cited

OTHER PUBLICATIONS

Jackson et al., Extracellular 2', 3'-cAMP is a Source of Adenosine, Journal of Biological Chemistry, Nov. 27, 2009, pp. 33097-33106, vol. 284, No. 48.

Jackson et al., The Extracellular Cyclic AMP-Adenosine Pathway in Renal Physiology, Annu. Rev. Physiol., 2004, pp. 571-599, vol. 66.

Jackson, Intraperitoneal Administration of Adenosine Inhibits Formation of Abdominal Adhesions, Diseases of the Colon & Rectum, 2004, pp. 1390-1396, vol. 47.

Jackson et al., Local and systemic effects of peritoneal lavage with high concentrations of adenosine in rats, Aliment Pharmacol Ther, 2000, pp. 1371-1380, vol. 14.

Jacobson et al., Table 1 of Chapter 6: Development of Selective Purinoceptor Agonists and Antagonists in Purinergic Approaches in Experimental Therapeutics (edited by K.A. Jacobson and M.F. Jarvis), 1997, 7 pages, Wiley-Liss, New York.

Jacobson et al., Chapter 6: P1 and P2 Purine and Pyrimidine Receptor Ligands in Purinergic and Pyrimidinergic Signalling I (Editors M.P. Abbracchio and M. Williams), 2001, 14 pages, Springer, Berlin.

Jansen et al., Failure of Peritoneal Irrigation with Heparin During Pelvic Operations upon Young Women to Reduce Adhesions, Surgery, Gynecology & Obstetrics, Feb. 1988, pp. 154-160, vol. 166.

Kapur et al., Oxyphenbutazone—Anti-inflammatory Agent—in Prevention of Peritoneal Adhesions, Arch Surg, Mar. 1969, pp. 301-302, vol. 98.

Li et al., The value of an absorbable adhesion barrier, Interceed®, in the prevention of adhesion reformation following microsurgical adhesiolysis, British Journal of Obstetrics and Gynaecology, Apr. 1994, pp. 335-339, vol. 101.

Magro et al., Expanded Polytetrafluoroethylene Surgical Membrane in Ovarian Surgery on the Rabbit (Biocompatibility, Adhesion Prevention Properties and Ability to Preserve Reproductive Capacity), The Journal of Reproductive Medicine, Feb. 1996, pp. 73-78, vol. 41, No. 2.

Mettler et al., Prospective Clinical Trial of SprayGel as a Barrier to Adhesion Formation: An Interim Analysis, The Journal of the American Association of Gynecologic Laparoscopists, Aug. 2003, pp. 339-344, vol. 10, No. 3.

Metwally et al., Fluid and pharmacological agents for adhesion prevention after gynaecological surgery, Cochrane Database of Systematic Reviews, 2006, 60 pages, Issue 2.

Monk et al., Adhesions after extensive gynecologic surgery: Clinical significance, etiology, and prevention, Am J Obstet Gynecol, 1994, pp. 1396-1403, vol. 170, No. 5, Part 1.

Noji et al., Adenosine uptake inhibitors, European Journal of Pharmacology, 2004, pp. 1-16, vol. 495.

O'Brien et al., Instruments & Methods: The Use of Ibuprofen and Dexamethasone in the Prevention of Postoperative Adhesion Formation, Obstetrics & Gynecology, Sep. 1982, pp. 373-378, vol. 60, No. 3.

Parker et al., The Scar-3 study: 5-year adhesion-related readmission risk following lower abdominal surgical procedures, Colorectal Disease, 2005, pp. 551-558, vol. 7.

Peters et al., a randomized clinical trial on the benefit of adhesiolysis in patients with intraperitoneal adhesions and chronic pelvic pain, British Journal of Obstetrics and Gynaecology, Jan. 1992, pp. 59-62, vol. 99.

Puchalski, the Influence of Cumulative Use of Dexamethasone, Promethazine and Dextran 70 as the Protection Against Creation of Intraperitoneal Adhesions on Selected Parameters of Humoral Resistance in Women Operated on Because of Mechanical Infertility, Ann. Acad. Med. Stetin., 1998, pp. 115-136, vol. 44.

Rappaport et al., Antibiotic Irrigation and the Formation of Intraabdominal Adhesions, The American Journal of Surgery, Nov. 1989, pp. 435-437, vol. 158.

Sekiba et al., Use of Interceed (TC7) Absorbable Adhesion Barrier to Reduce Postoperative Adhesion Reformation in Infertility and Endometriosis Surgery, Obstetrics & Gynecology, Apr. 1992, pp. 518-522, vol. 79, No. 4.

Troy, Editor, Remington: The Science and Practice of Pharmacy, 21st Edition, 2005, pp. 745-849, Lippincott Williams & Wilkins, Philadelphia.

Troy, Editor, Remington: The Science and Practice of Pharmacy, 21st Edition, 2005, pp. 946-953, Lippincott Williams & Wilkins, Philadelphia.

Van Der Krabben et al., Morbidity and mortality of inadvertent enterotomy during adhesiotomy, British Journal of Surgery, 2000, pp. 467-471, vol. 87.

Wiseman et al, The rates of adhesion development and the effects of crystalloid solutions on adhesion development in pelvic surgery, Fertility and Sterility, Oct. 1998, pp. 702-711, vol. 70, No. 4.

Yamagata et al., Specific Effect of Magnesium Ion on 2', 3'-Cyclic Amp Synthesis from Adenosine and Trimeta Phosphate in Aqueous Solution, Origins of Life and Evolution of the Biosphere, 1995, pp. 47-52, vol. 25.

Yoon et al., Effects on Retinal Adhesion of Temperature, Cyclic AMP, Cytochalasin, and Enzymes, Investigative Opthalmology & Visual Science, Jun. 1988, pp. 910-914, vol. 29, No. 6.

Zacharia et al., Adenosine and Inosine Prevent Abdominal Adhesions in a Mouse Model, The FASEB Journal, 2006, p. A1272, vol. 20.

CYCLIC ADENOSINE MONOPHOSPHATES FOR REDUCING THE FORMATION OF ADHESIONS

CROSS REFERENCE TO RELATED APPLICATIONS

This application is a National Stage of International Application No. PCT/US2009/063386, filed Nov. 5, 2009, which in turn claims the benefit of U.S. Provisional Patent Application No. 61/113,068, filed Nov. 10, 2008, which is incorporated herein by reference in its entirety.

Described herein are compositions and methods for reducing the formation of adhesions. In particular, compositions and methods are described for reducing the extent and severity of adhesions, for instance, post-surgical adhesion; and for tissue protection comprising by administration of cyclic adenosine monophosphate analogues and related compounds and compositions.

Adhesions are fibrous bands that form between tissues and organs as a result of an injury. Thus, adhesions are essentially internal scar tissue and occur naturally as a part of the body's healing processes. Unfortunately, adhesions can prevent tissues and organs from moving freely thus sometimes causing organs and tissues to become twisted or pulled from their normal positions. This results in pain and dysfunction and at times can be life-threatening.

Because adhesions can occur between and among many different surfaces of many different tissues and organs, there are many types of adhesions and these are associated with many types of morbidities. For example, adhesive capsulitis is due to adhesions between shoulder joint surfaces and results in restricted joint motion, a condition called "frozen shoulder." Adhesions often form after surgery, and such adhesions are called post-surgical adhesions. In this regard, abdominal adhesions are most commonly caused by abdominal surgical procedures, but may be caused also by pelvic inflammatory diseases such as endometriosis. Small bowel obstruction can occur when an adhesion kinks the small intestine and thereby prevents the moment of intestinal contents through the digestive tract. Importantly, small bowel obstruction secondary to post-surgical adhesion formation can occur decades after the initial surgical procedure. Small bowel obstruction is a medical emergence that can cause death, so immediate medical attention is required. A partial small bowel obstruction may respond to conservative medical intervention; however, sometimes re-operation to lyse the offending adhesion(s) or resect the affected small intestine is required. Surgery involving the uterus and uterine cavity can cause intrauterine adhesions, a condition called Asherman's Syndrome that can result in infertility.

Adhesions from previous surgeries can also make subsequent surgeries more difficult and dangerous. For example, prior post-surgical adhesions can obscure the surgeon's ability to see and gain access to tissues and organs in the surgical field. This is important because a majority of patients that undergo abdominal or pelvic surgery will be readmitted for surgery within ten years for related or unrelated conditions (Monk B J, Berman M L, Montz F J. Adhesions after extensive gynecologic surgery: clinical significance, etiology, and prevention. Am J Obstet. Gynec. 1994, volume 170, pages 1396-1403), and adhesions at reoperation significantly increase the risk of subsequent surgical procedures (Van der Krabben A A, Dijkstra F R, Nieuwenhuijzen M, Reijnen M M P J, Schaapveld M, Van Goor H. Morbidity and mortality of inadvertent enterotomy during adhesiotomy. Br J. Surg. 2000, volume 87, pages 467-471).

Adhesions are common. In the absence of adhesion barriers, adhesions occur in approximately 93% of all patients undergoing abdominal surgery. The National Hospital Discharge Survey of hospitalizations between 1998 and 2002 found that 51,100 of 281,982 hospitalizations were related to adhesions and adhesions were one of the associated problems for 227,882 other hospitalizations. Thus, during this time period in the United States alone, adhesions were directly or indirectly responsible for 948,000 hospital days, costing $1.18 billion. Patients undergoing lower abdominal surgery (excluding appendectomy) have a 5% risk of re-admission directly related to adhesions during the 5-year period following surgery (Parker M C, Wilson M S, Menzies D et al. The SCAR-3 study: 5-year adhesion-related readmission risk following lower abdominal surgical procedures. Colorectal Dis. 2005, volume 7, pages 551-558). A very high risk of an adhesion-related re-admission occurs in patients undergoing panproctocolectomy, ileostomy surgery or total colectomy procedures; however, the greatest risk burden for re-admission occurs following excision of the rectum, which is a common surgical procedure. Prior surgery has a major impact on patient outcome and re-admission risk is approximately doubled in patients who have undergone abdominal or pelvic surgery within the previous five years.

Attempts to develop anti-adhesion medications and devices have met with limited success. Many local and systemic anti-inflammatory drugs have been evaluated, yet none has been found effective in reducing post-surgical adhesions (Bateman B G, Nunley W C, Kitchin J D. Prevention of postoperative peritoneal adhesions with ibuprofen. Fertil Steril. 1982, volume 38, pages 107-108; Kapur B M, Talwar JR, Gulati S M. Oxyphenbutazone—anti-inflammatory agent—in the prevention of peritoneal adhesions. Arch Surg. 1969, volume 98, pages 301-302; O'Brien W F, Drake T S, Bibro M C. The use of ibuprofen and dexamethasone in the prevention of postoperative adhesion formation. Obstet. Gynecol. 1982, volume 60, pages 373-378; Puchalski A. The influence of cumulative dexamethasone, promethazine and dextran 70 used as protection against intraperitoneal adhesions on selected parameters of humoral immunity in women operated on for infertility. Ann Acad Med. Stetin. 1998, volume 44, pages 115-136).

Peritoneal lavage with antibiotic solutions also does not reduce adhesions and may in fact increase adhesion formation (Rappaport W D, Holcomb M, Valente J, Chvapil M. Antibiotic irrigation and the formation of intraabdominal adhesions. Am J. Surg. 1989, volume 158, pages 435-437).

"Hydrofloatation" with dextran 70 solutions, saline or Ringer's lactate, with or without heparin or corticosteroids, has been used to separate adjacent peritoneal surfaces but did not reduce adhesion formation (Rappaport W D, Holcomb M, Valente J, Chvapil M. Antibiotic irrigation and the formation of intraabdominal adhesions. Am J. Surg. 1989, volume 158, pages 435-437; Wiseman D M, Trout J R, Diamond M P. The rates of adhesion development and the effects of crystalloid solutions on the adhesion development in pelvic surgery. Fertil Steril. 1998, volume 70, pages 702-711; Metwally M, Watson A, Lilford R, Vandekerckhove P. Fluid and pharmacological agents for adhesion prevention after gynaecological surgery. Cochrane Database Syst Rev. 2006).

Icodextrin 4% solution (Adept® Adhesion Reduction Solution, Baxter Healthcare Corp., Deerfield, Ill.), a water-soluble, high molecular weight, glucose polymer in an electrolyte solution, can be used as a peritoneal instillate (1-1.5 L) and functions as a colloid osmotic agent to retain fluid within the peritoneal cavity for up to 4 days. A preliminary randomized, controlled pilot study reported that icodextrin 4% reduced adhesion formation (diZerega G S, Verco S J S, Young P, et al. A randomized, controlled pilot study of the safety and efficacy of 4% icodextrin solution in the reduction of adhesions following laparoscopic gynaecological surgery. Hum Reprod. 2002, volume 17, page 1031-1038). However there is insufficient evidence for the use of icodextrin 4% as an adhesion-preventing agent (Metwally M, Watson A, Lilford R, Vandekerckhove P. Fluid and pharmacological agents for adhesion prevention after gynaecological surgery, Cochrane Database Syst Rev. 2006). The Food and Drug Administration (FDA) has approved icodextrin 4% for the reduction of postoperative adhesions in patients undergoing gynecologic laparoscopic adhesiolysis.

Theoretically, heparin should decrease adhesion formation by inhibiting coagulation and promoting fibrinolysis (Al-Chalabi H A, Otubo J A. Value of a single intraperitoneal dose of heparin in prevention of adhesion formation: an experimental evaluation in rats. Int J. Fertil. 1987, volume 32, pages 332-335); however, peritoneal irrigation with heparin solution did not reduce peritoneal adhesions in women after pelvic surgery (Jansen R P. Failure of peritoneal irrigation with heparin during pelvic operations upon young women to reduce adhesions. Surg Gynecol Obstet. 1988, volume 166, pages 154-160).

Several "surgical barriers" have been evaluated to prevent post-surgical adhesions. Sodium hyaluronic acid (HA) and carboxymethylcellulose (CMC) are combined in a bioresorbable membrane (Seprafilm®; Genzyme, Cambridge, Mass.). CMC is nontoxic and the HA film is a transparent, absorbable membrane that separates opposing tissue surfaces for several days. In a small study of patients undergoing open-abdominal myomectomy, patients randomized to HA film had fewer adhesions than controls (Diamond M P, Reduction of adhesions after uterine myomectomy by Seprafilm membrane (HAL-F): a blinded, prospective, randomized, multicenter clinical study. Fertil Steril. 1996, volume 66, pages 904-910). Unfortunately, there is limited evidence for the effectiveness of HA film for preventing adhesion formation after myomectomy (Farquhar C, Vandekerckhove P, Watson A, Vail A, Wiseman D. Barrier agents for preventing adhesions after surgery for subfertility, Cochrane Database Syst Rev. 2000). HA film may also reduce midline adhesions (Peters A A, Trimbos-Kemper G C, Admiraal C, Trimbos J B, Hermans J. A randomized clinical trial on the benefits of adhesiolysis in patients with intraperitoneal adhesions and chronic pelvic pain. Br J Obstet. Gynaecol. 1992, volume 99, pages 59-62). However, a very large multicenter trial involving patients randomized to HA film or no treatment at time of intestinal resection reported no effect of HA film on the rate of small bowel obstruction (Fazio V W, Cohen Z, Fleshman J W et al., Reduction in adhesive small-bowel obstruction by seprafilm adhesion barrier after intestinal resection. Dis Colon Rectum. 2006, volume 49, pages 1-11). HA film has been approved by the FDA, but because it breaks apart easily, HA film is restricted to use during laparotomy.

Oxidized regenerated cellulose (Interceed®; ETHICON Women's Health and Urology, Somerville, N.J.) is another adhesion barrier. Oxidized regenerated cellulose is degraded into monosaccharides within approximately 2 weeks after application, and has been reported to decrease adhesion formation in several randomized controlled clinical trials (INTERCEED(TC7) Adhesion Barrier Study Group, Prevention of postsurgical adhesions by Interceed(TC7), an absorbable adhesion barrier: a prospective randomized multicenter clinical study. Fertil Steril. 1989, volume 51, pages 933-938; Sekiba K and The Obstetrics and Gynecology Adhesion Prevention Committee, Use of Interceed(TC7) absorbable adhesion barrier to reduce postoperative adhesion reformation in infertility and endometriosis surgery. Obstet. Gynecol. 1992, volume 79, pages 518-522; Azziz R and The INTERCEED (TC7) Adhesion Barrier Study Group II. Microsurgery alone or with INTERCEED Absorbable Adhesion Barrier for pelvic sidewall adhesion re-formation. Surg Gynecol Obstet. 1993, volume 177 (1993), pages 135-139; Li T C, Cooke I D. The value of an absorbable adhesion barrier, Interceed, in the prevention of adhesion reformation following microsurgical adhesiolysis. Br J Obstet. Gynaecol. 1994, volume 101, pages 335-339; Franklin R R and The Ovarian Adhesion Study Group. Reduction of ovarian adhesions by the use of Interceed. Obstet. Gynecol. 1995, volume 86, pages335-340). Although oxidized regenerated cellulose reduces the incidence and extent of new and recurrent adhesions by 50%-60% after both laparoscopic and open-abdominal surgical procedures, there is little evidence that the substance improves fertility. The FDA has approved oxidized regenerated cellulose (Interceed®) for reducing adhesions, but only for open-abdominal surgery.

Expanded polytetrafluoroethylene (ePTFE, Gore-Tex Surgical Membrane®; W.L. Gore Corp., Flagstaff, Ariz.) is a nonabsorbable adhesion barrier that must be sutured to tissue and can reduce adhesion formation (Magro B, Mita P, Bracco G L, Coccia E, Scarselli G. Expanded poly-tetrafluoroethylene surgical membrane in ovarian surgery on the rabbit (biocompatibility, adhesion prevention properties and ability to preserve reproductive capacity). J Reprod Med. 1996, volume 41, pages 73-78). ePTFE decreases postmyomectomy adhesions and pelvic sidewall adhesions (Haney A F, Hesla J, Hurst B S et al. Expanded polytetrafluoroethylene (ePTFE) (Gore-Tex Surgical Membrane) is superior to oxidized regenerated cellulose (Interceed TC7+) in preventing adhesions. Fertil Steril. 1995, volume 63, pages 1021-1026). Although ePTFE has been approved by the FDA for use in the United States for peritoneal repair and although ePTFE may be more effective than oxidized regenerated cellulose in preventing adhesion formation, the use of ePTFE has been limited by the need for suturing and later reoperation for removal.

Hyaluronic acid solution (Sepracoat®; Genzyme, Cambridge, Mass.), a bioabsorbable component of the extracellular matrix, is yet another anti-adhesion product. In patients undergoing open gynecologic procedures, HA solution reduced adhesion formation, particularly in areas of indirect trauma, and resulted in a increase in the likelihood of having at least one adhesion-free ovary (Diamond MP and The Sepracoat Adhesion Study Group. Reduction of de novo postsurgical adhesions by intraoperative precoating with Sepracoat (HAL-C) solution: a prospective, randomized, blinded, placebo-controlled multicenter study. Fertil Steril. 1998, volume 69, pages 1067-1074). An FDA advisory panel unanimously rejected the approval of HA solution; however it is approved in Europe.

Polyethylene glycol (PEG) (Spraygel®; Confluent Surgical, Waltham, Mass.) is a two-component system comprised of two PEG-based liquids that are delivered via a system consisting of an air pump and spray applicator. The system dispenses a blue-colored PEG that covers the serosal defects, and shortly after application, the PEG becomes a gel that sticks to tissues. Although PEG showed efficacy in early clinical trials (Mettler L, Audebert A, Lehmann-Willenbrock E, Schive K, Jacobs VR. Prospective clinical trial of SprayGel as a barrier to adhesion formation: an interim analysis. J Am Assoc Gynecol Laparosc. 2003, volume 10, pages 339-344), larger studies are required to evaluate its effectiveness, and PEG has not been approved by the FDA.

Fibrin sealant (Tisseel VH®; Baxter Healthcare Corp., Deerfield, Ill.) is yet another adhesion-reducing product. Although in animals treatment of peritoneal defects with fibrin sealant decreased intra-abdominal adhesion formation and reformation (Caballero J, Tulandi T. Effects of Ringer's lactate and fibrin glue on postsurgical adhesions. J Reprod Med. 1992, volume 37, pages 141-143), clinical data regarding the efficacy of fibrin sealant in prevention of adhesions are limited. Unfortunately, because fibrin sealant is a biological product derived from human blood donors, it poses a risk for transmission of infectious agents. The FDA has approved Fibrin sealant, but for the use as an adjunct to hemostasis in cardiothoracic surgery and the surgical treatment of splenic injuries, and as an adjunct for the closure of colostomies.

U.S. Pat. No. 6,566,371, to Jackson, discloses use of adenosine esters and adenosine-releasing prodrugs, including adenosine 3':5' cyclic-monophosphate, to prevent adhesions. While certainly effective in reducing adhesions, there remains a need for compounds and/or treatment modalities that effectively reduce postoperative adhesions.

In summary, post-surgical adhesions remain a serious, prevalent, unsolved clinical problem. Post-surgical adhesions may result in infertility, pain and bowel obstruction. Although strict adherence to surgical principles helps reduce postoperative adhesions, there remains a great need for improved products, especially those that can be delivered during minimally invasive surgery. There is no evidence that anti-inflammatory agents reduce postoperative adhesions. Although some surgical barriers reduce post-surgical adhesions, these produces are difficult to use and are not approved for minimally invasive surgery. Also, there is no substantial evidence that the use of FDA approved anti-adhesion products improves fertility, reduces pain or decreases the incidence of small bowel obstruction. Clearly, novel treatments for the prevention of post-surgical adhesions and tissue protection are badly needed, particularly those that can be easily and conveniently administered as a solution during minimally-invasive surgery and that can reach and protect tissues both within the surgical field view as well as those hidden from view.

SUMMARY

Disclosed herein is the use of cyclic adenosine monophosphates for the reduction of adhesions. A specific, non-limiting example of a cyclic adenosine monophosphate for reducing adhesion formation is 2',3'-cyclic adenosine monophosphate; however other derivatives of this cyclic adenosine monophosphate by substitution in the ribose ring or adenine purine base, or both, are also disclosed, along with pharmaceutically acceptable salts thereof. In particular, cyclic adenosine monophosphates in which the adenosine moiety is substituted to yield adenosine analogues (as described below) of cyclic adenosine monophosphates are disclosed. The cyclic adenosine monophosphates can be applied locally in the tissue field where adhesion formation or injury may occur, will occur or has occurred. Alternatively, the cyclic adenosine monophosphates can be administered systemically. Administration may occur before tissue injury, during tissue injury or after tissue injury. Administration may be applied once or multiple times as medically required. The application of the cyclic adenosine monophosphates will not only reduce adhesion formation, but also attenuate tissue injury and provide for tissue protection.

A method of reducing the formation of adhesions in a mammalian subject is provided. The method comprises administering to the subject one or more compounds chosen from 2',3'-cyclic adenosine monophosphate, analogues thereof, and pharmaceutically acceptable salts thereof, able to reduce the formation of adhesions in a subject as compared to adenosine monophosphate, wherein the one or more compounds chosen from 2',3'-cyclic adenosine monophosphate, analogues thereof, and pharmaceutically acceptable salts thereof, is administered to the subject in an amount effective to reduce adhesions in the subject. In one non-limiting embodiment the compound is 2',3'-cyclic adenosine monophosphate or a pharmaceutically acceptable salt thereof. In another, the compound is an analogue of 2',3'-cyclic adenosine monophosphate or a pharmaceutically acceptable salt thereof able to reduce the formation of adhesions in a subject as compared to adenosine monophosphate. An analogue of 2',3'-cyclic adenosine monophosphate may be modified in one or both of an adenine portion or a ribose portion of the 2',3'-cyclic adenosine monophosphate. For example and without limitation, the adenine portion may be modified at one or more of its 1, 2, 3, N(6) or 8 position, as described herein. In one embodiment, the mammalian subject is a human. The adhesions may result from a surgical procedure (surgery) to the subject's abdomen or pelvic region.

According to another embodiment, a method of reducing inflammation or tissue damage in a mammalian subject after abdominal or pelvic surgery is provided. The method comprises administering to the subject one or more compounds chosen from 2',3'-cyclic adenosine monophosphate, analogues thereof, and pharmaceutically acceptable salts thereof able to reduce inflammation or tissue damage in a subject as compared to adenosine monophosphate, wherein the one or more compounds chosen from 2',3'-cyclic adenosine monophosphate, analogues thereof, and pharmaceutically acceptable salts thereof, is administered to the subject in an amount effective to reduce inflammation or tissue damage. The one or more compounds chosen from 2',3'-cyclic adenosine monophosphate, analogues thereof, and pharmaceutically acceptable salts thereof may be any one or more compounds chosen from 2',3'-cyclic adenosine monophosphate, analogues thereof, and pharmaceutically acceptable salts thereof described herein.

Also provided herein is the use of one or more compounds chosen from 2',3'-cyclic adenosine monophosphate, analogues thereof, and pharmaceutically acceptable salts thereof, able to reduce the formation of adhesions in a subject as compared to adenosine monophosphate, in the manufacture of a medicament for reducing the formation of adhesions in a mammalian subject or reducing inflammation or tissue damage in a mammalian subject after abdominal or pelvic surgery.

BRIEF DESCRIPTION OF THE DRAWINGS

FIG. 1A shows the adenine (A) and sugar (B) portions of the compound, while FIG. 1B shows a numbering scheme for the compound.

FIGS. 2A and 2B provided non-limiting examples of 2',3'-cyclic adenosine monophosphate analogues. FIG. 2A provides a structure of a phosphorothioate analogue, while

DETAILED DESCRIPTION

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of these ranges is intended as a continuous range including every value between the minimum and maximum values. For definitions provided herein, those definitions also refer to word forms, cognates and grammatical variants of those words or phrases.

A "drug product" is a compound, composition, formulation, etc. as is understood in the medical and pharmaceutical arts. Drug products comprise an "active agent" which is a compound or composition that has a specific pharmacological effect. A drug product is preferable "pharmaceutically acceptable," meaning that it is suitable for administration to a subject for a stated purpose, which is typically referred to as an "indication". Irrespective of whether a drug product or other composition, compound or material may or may not cause harm by its administration to a subject, it may be "pharmaceutically acceptable" if benefits of the composition, compound, material or drug product outweigh its risks. In one aspect, a compound, composition, material, excipient or drug product is pharmaceutically acceptable if it meets the requirements of an applicable regulatory agency, such as the US Food and Drug Administration, or any other applicable regulatory body, which includes compounds, compositions, materials or drug products that are Generally Recognized As Safe (GRAS). In a broader sense, a composition, compound, material or drug product and it is material is not biologically or otherwise undesirable for its intended use, that is, the material can be administered to an individual along with the relevant active compound without causing clinically unacceptable biological effects or interacting in a deleterious manner with any of the other components of the pharmaceutical composition in which it is contained.

Throughout the description and claims of this specification the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions.

As used throughout, by a "subject" is meant an animal or human. Thus, the "subject" can include domesticated animals, such as cats, dogs, etc., livestock (e.g., cattle, horses, pigs, sheep, goats, etc.), laboratory animals (e.g., mouse, rabbit, rat, guinea pig, etc.) and birds. In one aspect, the subject is a mammal such as a primate or a human, including patients.

Figure 1A:
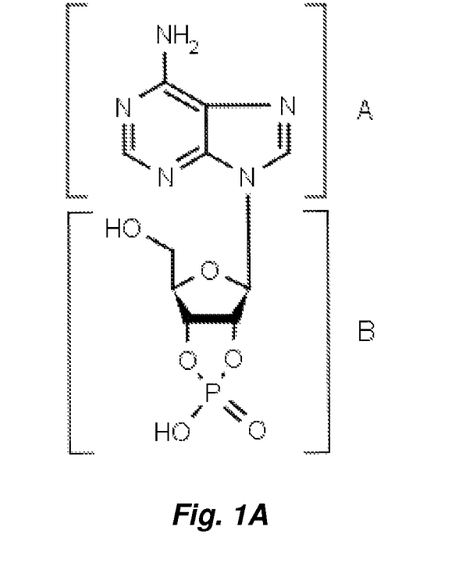
FIGS. 1A and 1B provide the structure of 2',3'-cyclic adenosine monophosphate.
Figure 1B:
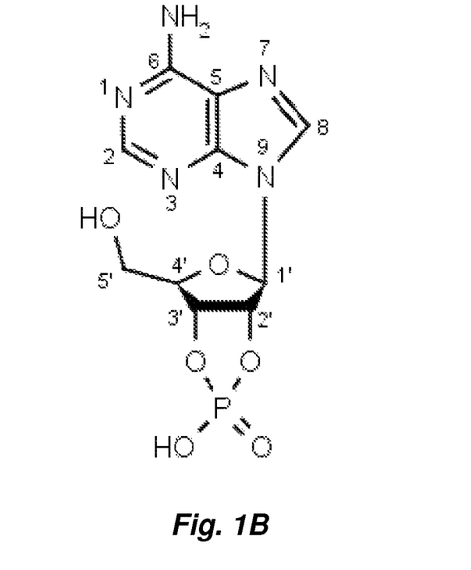
Figure 1C:
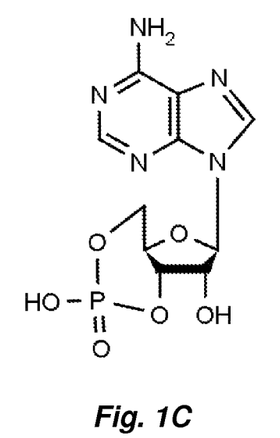
FIG. 1C provides the structure for 3',5' cyclic adenosine monophosphate.
Figure 2A:
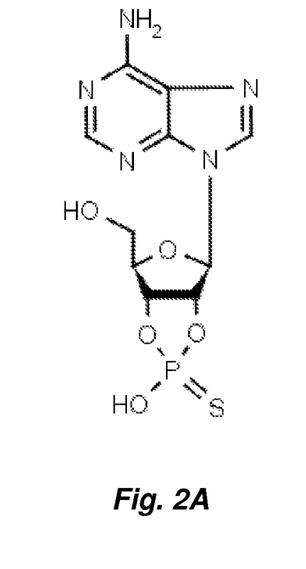

As described herein, the terms "adenosine analogue" and "analogue" referred to in describing cyclic adenosine monophosphates refer to any chemical derivative of adenosine. Adenosine comprises adenine attached to ribose. FIG. 1A provides a structure of 2',3'-cyclic adenosine monophosphate, with conventional ring-numbering scheme for the adenine and ribose portions of the compound. FIG. 1C depicts 3',5'-cyclic adenosine monophosphate. Thus an adenosine analogue comprises an analogue of ribose and/or an adenine analogue. In one non-limiting embodiment, the adenosine analogue is 2',3'-cyclic adenosine monophosphate or a 2',3' cyclic pentose analogue of 2',3' cyclic adenosine monophosphate. A 2',3' cyclic pentose analogue of 2',3' cyclic adenosine monophosphate is a compound in which the adenine (base) portion (e.g., bracketed portion A of the structure depicted in FIG. 1A) and/or the ribose (sugar) portion (e.g., bracketed portion B of the structure depicted in FIG. 1A) of 2',3' cyclic adenosine monophosphate is modified. In cases where the adenine portion is modified, the adenine of 2',3' cyclic adenosine monophosphate is mono-substituted, meaning the adenine portion comprises a singly-substituted adenine, such as N(6)-benzoyl adenine. In cases where the ribose portion is modified, the 2',3' ribose cyclic monophosphate portion of 2',3' cyclic adenosine monophosphate is a 2',3' cyclic monophosphate, other than 2',3' ribose cyclic monophosphate. Examples include furanose form of ribose, arabinose, xylose and lyxose, or a stereoisomer thereof, including functional equivalents to the cyclic monophosphate portion of the sugar, such phosphorothioate (see, e.g., FIG. 2A). Both the sugar portion and the base portion of 2',3' cyclic adenosine monophosphate may be modified, so long as functionality is retained.

A pentose analogue can comprise many different chemical derivatives of ribose. In one non-limiting embodiment, the pentose analogue contains one or more sulfur groups as compared to ribose, such as in 4'-thioadenosine and 5'-methylthioadenosine. In another non-limiting embodiment, the pentose analogue lacks one or more oxygen groups as compared to ribose, such as N(6)-monobutyryl-2'-deoxycyclic adenosine monophosphate; 5'-deoxycyclic adenosine; 2'-deoxyadenosine 3',5'-cyclic monophosphate; and 5'-deoxy-5'-(methylthio)adenosine.

Adenine analogues include many different chemical derivatives of adenine with one or more substitutions in the adenine structure. In one non-limiting embodiment, the adenine analogue comprises replacing one or more functional groups of adenine with another functional group. For example and without limitation, the N(6) amino group on adenine can be replaced with another functional group (collectively "N(6) adenine analogues"), as in 6-chloropurine riboside; 6-cyanopurine; 6-ethoxypurine; 6-ethylmercaptopurine; and 6-methylpurine. In another non-limiting example, the adenine analogue is N(6)-substituted, meaning the adenine portion is modified at its N(6) position with, for example an without limitation, lower alkyl ($C_{1-6}$ straight or branched chain alkyl); lower alkoxyl ($C_{1-6}$ straight or branched chain alkoxyl); lower alkenyl ($C_{1-6}$ straight, ring or branched chain alkenyl); aryl, optionally comprising one or more $C_{1-4}$ alkyl substitutions, such as methyl, ethyl, propyl butyl, t-butyl, or halo (Cl, F, I or Br) groups); furfuryl (as in kinetin riboside); phenylisopropyl; 4-[2-[[4-[2-[(2-aminoethyl)amino]-2-oxoethyl]phenyl]amino]-2-oxoethyl]phenyl; cyclopentyl; hydroxycyclopentyl; cyclohexyl; 2-(benzylthiazoylyl)thio-2-propyl; 1-methyl-2-phenylethyl; p-(carboxyethyl)phenylethylamino; 2-2-(3,5-dimethoxyphenyl)-2-(2-methylphenyl)ethyl; 2-[4-(2-(2-(4-aminophenyl)methylcarbonylamino)ethylaminocarbonyl)ethyl)phenyl)ethylamino]; 1-[6-amino-2-(1-hexynyl); 1-[6-[[3-(iodophenyl)methyl]amino; 1-[2-chloro-6-[[(3-iodophenyl)methyl]amino]; (4-aminophenyl)ethyl; 4-amino-3-iodobenzyl; 1-(3-chlorothiophen-2-yl)butan-2-yl; methylbenzyl, diphenylethyl, benzoyl; butyryl; hexyl; methyl; phenoxyacetyl; isopentenyl; dimethylallyl; ethane; or 7-hydroxy-2-imidazo.

In one non-limiting embodiment, the adenine analogue comprises functional groups on the adenine portion, such as: 1-methyl; and 3-methyl. In another non-limiting embodiment, the adenine analogue comprises functional groups on the carbon groups of the adenine rings, such as, without limitation: 8-halo, 8-chloro; 8-bromo; 2-halo; 2-chloro;

8-methylamino; 8-(4-chlorophenyl)thio; 8-piperidino; 8-thio-benzyl; 8-methylthioe; and 8-chloroacetylaminoethylthio.

Figure 2B:
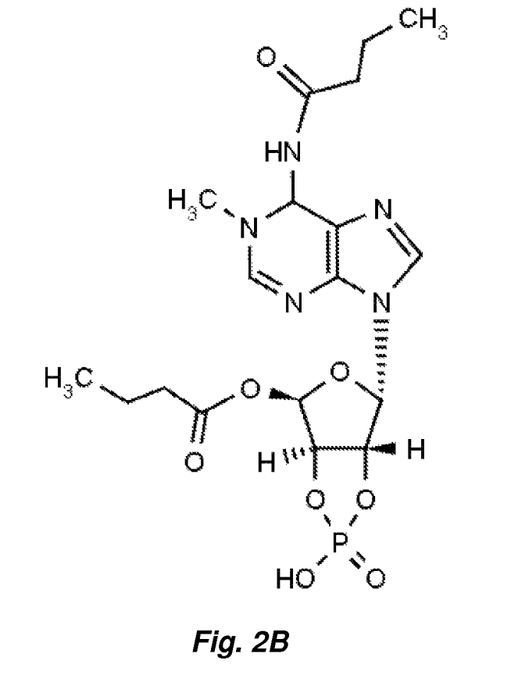
FIG. 2B shows a di-butanoyl analogue.

The adenosine analogue can comprise one or more different functional groups on both the adenine and ribose portions, such as in the 5'-(ribose portion) and N(6)-(adenine portion)-substituted analogues Bucladesine (butanoyl, see FIG. 2B); and disuccinyl-substituted 2',3'-cyclic adenosine monophosphate.

Further examples of adenosine analogs are listed in Table 1 of Chapter 6 (pages 104 through 107) by K. A. Jacobson and A. M. Van Rhee in Purinergic Approaches in Experimental Therapeutics (edited by K. A. Jacobson and M. F. Jarvis, Wiley-Liss, New York, 1997) and in Chapter 6 (pages 130-140) by K. A. Jacobson and L. J. S. Knutsen in Purinergic and Pyrimidinergic Signalling I (editors M. P. Abbracchio and M. Williams, Springer, Berlin, 2001).

Analogues of 2',3'-cyclic adenosine monophosphate are analogues in the sense that they have the ability to prevent abdominal adhesion formation substantially as described herein for 2',3'-cyclic adenosine monophosphate, though the reduction may be to a greater or lesser extent as compared to 2',3'-cyclic adenosine monophosphate. More specifically, they are able to reduce the number of adhesions as determined by any useful end-point, for example and without limitation, the semi-quatitative method shown in the Example below. For purposes herein, any analogue of 2',3'-cyclic adenosine monophosphate has the ability to reduce adhesion formation to a statistically significant extent (according to any clinically-acceptable standard) by any acceptable assay and end point.

Our previous published studies have shown that adenosine added to the peritoneal cavity can inhibit surgically-induced abdominal adhesion formation in both rats (Jackson E K. Intraperitoneal administration of adenosine inhibits formation of abdominal adhesions. Dis Colon Rectum. 2004, volume 47, pages: 1390-1396; Jackson E K. Intraperitoneal administration of adenosine for the treatment of prevention of gastrointestinal of systemic diseases. 2003, U.S. Pat. No. 6,566,371) and mice (Zacharia L, Jackson, E K. Adenosine prevents abdominal adhesions in a mouse model. FASEB Journal. 2005, page A759). However, there are serious limitations with regard to using adenosine for this purpose that preclude an optimal anti-adhesive efficacy. First, the aqueous solubility of adenosine is limited, and we have been unable to prepare stable aqueous solutions of adenosine with concentrations above 23 millimoles/L. In addition, because adenosine is rapidly taken up by cells (Noji T, Karasawa A, Kusaka H. Adenosine uptake inhibitors. Eur J. Pharmacol. 2004, volume 495, pages 1-14) and metabolized to inosine by adenosine deaminase (Noji T, Karasawa A, Kusaka H. Adenosine uptake inhibitors. Eur J. Pharmacol. 2004, volume 495, pages 1-14), adenosine added to the peritoneal cavity would be expected to disappear rapidly, and indeed in rats the half-life of adenosine in the peritoneal cavity after the adenosine is added to the peritoneal cavity is only about 15 minutes (Jackson E K. Intraperitoneal administration of adenosine inhibits formation of abdominal adhesions. Dis Colon Rectum. 2004, volume 47, pages: 1390-1396). Consequently the time-concentration profile of adenosine in the surgical field cannot be optimized. Therefore, we considered that a highly water-soluble, adenosine prodrug that is restricted to the extracellular space but can be converted directly to adenosine via a single enzyme-mediated step would have improved efficacy relative to adenosine to prevent post-surgical abdominal adhesions when added to the peritoneal cavity because a higher concentration could be delivered to the surgical space, the compound would not be taken up by cells and yet the prodrug would none-the-less be converted to adenosine for efficacy. Because 5'-adenosine monophosphate is highly water soluble (stable aqueous solutions in excess of 75 millimoles/L can be obtained readily), is not membrane-permeable and is well known to be converted to adenosine in the extracellular space by ecto-5'-nucleotidase (Hunsucker S A, Mitchell B S, Spychala J. The 5'-nucleotidases as regulators of nucleotide and drug metabolism. Pharmacology & Therapeutics. 2005, volume 107, pages 1-30), we predicted that 5'-adenosine monophosphate would be more efficacious than adenosine with regard to inhibiting surgically-induced abdominal adhesions. Indeed, our previous studies showed that addition of 5'-adenosine monophosphate to the abdominal cavity of rats achieves high levels of adenosine in the intestinal circulation (Jackson E K, Swamy R S, Herzer W A, Mi Z. Local and systemic effects of peritoneal lavage with high concentrations of adenosine. Aliment Pharmacol Ther. 2000, volume 14, pages 1371-1380).

Although 3',5'-cyclic adenosine monophosphate also is highly water soluble, does not penetrate cell membranes and can be converted in the extracellular space to adenosine, its extracellular conversion to adenosine requires two metabolic steps, first to 5'-adenosine monophosphate mediated by ecto-3',5'-cyclic adenosine monophosphate phosphodiesterase and then to adenosine via ecto-5'-nucleotidase (Jackson E K, Dubey R K. The extracellular cyclic AMP-adenosine pathway in renal physiology. Annual Review of Physiology 2004, volume 66, pages 571-599). Therefore, we predicted that 3',5'-cyclic adenosine monophosphate would be less efficacious than either 5'-adenosine monophosphate or adenosine because it would not be converted efficiently to adenosine. Moreover, we also predicted that 2',3'-cyclic adenosine monophosphate (a positional isomer of 3',5'-cyclic adenosine monophosphate), which is not known to be metabolized extracellularly in the peritoneum to adenosine, would be inactive. We also predicted that unlike 5'-adenosine monophosphate, neither 2'-adenosine monophosphate nor 3'-adenosine monophosphate would be active because these are not known to be metabolized extracellularly to adenosine in the peritoneum. We only recently have found that 2',3'-cyclic adenosine monophosphate can be metabolized extracellularly in kidneys to adenosine (Jackson et al. Extracellular 2',3'-cAMP is a Source of Adenosine, JBC Papers in Press. Published on Oct. 1, 2009 as Manuscript M109.053876), but there remains no evidence of such a pathway in the peritoneum. Importantly, as demonstrated in the example described in detail below, most of these key predictions were totally incorrect and the experiments yielded unanticipated and surprising results. As indicated below, the effects of 2',3'-cAMP are not mimicked by 2'-AMP or 3'-AMP, and the effects of 2',3'-cAMP are not blocked by an adenosine receptor antagonist.

As predicted, at a concentration of 75 millimoles/L, both 2'-adenosine monophosphate and 3'-adenosine monophosphate were nearly inactive; but surprisingly 5'-adenosine monophosphate, which is a direct prodrug of adenosine because it requires only a single metabolic step to be converted to adenosine, also was nearly inactive. Also surprising was the finding that 3',5'-cyclic adenosine monophosphate (75 millimoles/L) was as efficacious as adenosine and more efficacious than 5'-adenosine monophosphate with respect to inhibiting the formation of post-surgical abdominal adhesions. Most surprising was the result with 2',3'-cyclic adenosine monophosphate, a compound that, unlike 3',5'-cyclic adenosine monophosphate, is not known to be metabolized to adenosine.

In this regard, 2',3'-cyclic adenosine monophosphate at 75 millimoles/L was highly effective and exceeded the efficacy of even adenosine and 3',5'-cyclic adenosine monophosphate. Thus our results described in detail below indicate that cyclic adenosine monophosphates have unexpected efficacy with regard to inhibiting adhesion formation and protecting tissues from injury that is unanticipated and difficult to explain based on conversion to their corresponding non-cyclic adenosine monophosphates because the corresponding non-cyclic adenosine monophosphates are practically inactive.

Without wishing to be limited by theory, the efficacy of cyclic adenosine monophosphates in attenuating adhesion formation and protecting tissues from injury also cannot be ascribed to direct activation of intracellular proteins (such as protein kinase A) because the cyclic adenosine monophosphates used in the study described below are highly polar and would not penetrate cell membranes. Moreover, it is well-known that protein kinase A is activated by intracellular 3',5'-cyclic adenosine monophosphate, but not by 2',3'-cyclic adenosine monophosphate. The mechanism, therefore, by which the cyclic adenosine monophosphates inhibit adhesion formation and afford tissue protection is at present unknown.

Based on these results, disclosed herein is the use of cyclic adenosine monophosphates for the reduction of adhesions and tissue damage and/or inflammation. Specific examples of cyclic adenosine monophosphates for reducing adhesion formation include 3',5'-cyclic adenosine monophosphate and 2',3'-cyclic adenosine monophosphate; however other derivatives of these two cyclic adenosine monophosphates by substitution in the ribose ring or adenine purine base or both are also disclosed. In particular, cyclic adenosine monophosphates in which the adenosine moiety is substituted to yield adenosine analogues (as defined above) of cyclic adenosine monophosphates are disclosed. The cyclic adenosine monophosphates can be applied locally in the tissue field where adhesion formation or injury may occur, will occur or has occurred. Alternatively, the cyclic adenosine monophosphates can be administered systemically. Administration may occur before tissue injury, during tissue injury or after tissue injury. Administration may be applied once or multiple times as medically required. The application of the cyclic adenosine monophosphates will not only reduce adhesion formation, but also will attenuate tissue injury and provide for tissue protection. As indicated below, on visual inspection the abdominal contents in mice treated with 2',3'-cAMP appeared less inflamed and generally healthier than the abdominal contents of mice treated with other compounds. Thus, it appeared that 2',3'-cAMP also reduced tissue damage and/or inflammation.

Veterinary use of the methods described herein is also anticipated. In this regard, cyclic adenosine monophosphates thereof may be administered to for example dogs, cats, horses, cattle, sheep and pigs to prevent the formation of adhesions and for tissue protection.

Although the methods described herein are primarily focused on use of cyclic adenosine monophosphates to prevent adhesions and tissue injury associated with surgery, the use of cyclic adenosine monophosphates to prevent adhesion formation and tissue injury from any cause, whether mechanical, chemical, biological or due to any disease process, is also contemplated.

Although the methods described herein are primarily addressed to use of a cyclic adenosine monophosphate added to the surgical field, the administration of a cyclic adenosine monophosphate by any route (for example, orally, intravenously or into or onto the mouth, nose, ears, skin, rectum, vagina, uterus, pelvic cavity, abdominal cavity, thoracic cavity, joint spaces, eyes, urethra, bladder, ureter or any other body cavity or space) is also contemplated and is encompassed by this disclosure. Also contemplated and encompassed by the present disclosure is the use of a cyclic adenosine monophosphate in either open-field surgery or minimally-invasive surgery of any type and on any anatomical structure.

In use, the cyclic adenosine monophosphate may be admixed with any pharmaceutically acceptable carrier or carriers, such as water, saline, physiological salt solutions, Ringer's solution or any other carrier customarily used for administration of drugs to the subject in question (see, generally, Troy, D B, Editor, Remington: The Science and Practice of Pharmacy, $21^{st}$ Ed., Lippincott Williams & Wilkins (2005), pp. 745-849 for descriptions of various compositions, solutions, and dosage forms useful for administration of the described cyclic adenosine monophosphates, as well as methods of making such compositions, solutions, and dosage forms).

Pharmaceutically acceptable salts of the cyclic adenosine monophosphate also may be used in the methods described herein. Pharmaceutically acceptable salt forms of the compounds described herein may be prepared by conventional methods known in the pharmaceutical arts. For example and without limitation, where a compound comprises a carboxylic acid group, a suitable salt thereof may be formed by reacting the compound with an appropriate base to provide the corresponding base addition salt. Non-limiting examples include: alkali metal hydroxides, such as potassium hydroxide, sodium hydroxide and lithium hydroxide; alkaline earth metal hydroxides, such as barium hydroxide and calcium hydroxide; alkali metal alkoxides, such as potassium ethanolate and sodium propanolate; and various organic bases such as piperidine, diethanolamine, and N-methylglutamine.

Acid addition salts may be prepared by treating a compound with pharmaceutically acceptable organic and inorganic acids, including, without limitation: hydrohalides, such as hydrochloride, hydrobromide, hydroiodide; other mineral acids and their corresponding salts such as sulfates, nitrates, and phosphates; alkyl- and mono-arylsulfonates, such as ethanesulfonate, toluenesulfonate, and benzenesulfonate; and other organic acids and their corresponding salts, such as acetate, tartrate, maleate, succinate, citrate, benzoate, salicylate, and ascorbate.

Thus, non-limiting examples of pharmaceutically-acceptable base salts include: aluminum, ammonium, calcium, copper, ferric, ferrous, lithium, magnesium, manganic, manganous, potassium, sodium, and zinc salts. Salts derived from pharmaceutically acceptable organic non-toxic bases include, without limitation: salts of primary, secondary, and tertiary amines, substituted amines including naturally occurring substituted amines, cyclic amines, and basic ion exchange resins, such as arginine, betaine, caffeine, chloroprocaine, choline, N,N'-dibenzylethylenediamine (benzathine), dicyclohexylamine, diethanolamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine, and tris-(hydroxymethyl)-methylamine (tromethamine).

Non-limiting examples of pharmaceutically-acceptable acid salts include: acetate, adipate, alginate, arginate, aspartate, benzoate, besylate (benzenesulfonate), bisulfate, bisulfite, bromide, butyrate, camphorate, camphorsulfonate, caprylate, chloride, chlorobenzoate, citrate, cyclopentanepropionate, digluconate, dihydrogenphosphate, dinitrobenzoate, dodecylsulfate, ethanesulfonate, fumarate, galacterate, galacturonate, glucoheptanoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, iso-butyrate, lactate, lactobionate, malate, maleate, malonate, mandelate, metaphosphate, methanesulfonate, methylbenzoate, monohydrogenphosphate, 2-naphthalenesulfonate, nicotinate, nitrate, oxalate, oleate, pamoate, pectinate, persulfate, phenylacetate, 3-phenylpropionate, phosphate, phosphonate, and phthalate.

Compounds comprising basic nitrogen-containing groups may be quaternized with such agents as $C_1$-$C_4$ alkyl halides, such as methyl, ethyl, iso-propyl and tert-butyl chlorides, bromides and iodides; $C_1$-$C_4$ alkyl sulfate such as dimethyl, diethyl and diamyl sulfates; $C_{10}$-$C_{18}$ alkyl halides, such as decyl, dodecyl, lauryl, myristyl and stearyl chlorides, bromides and iodides; and aryl-$C_1$-$C_4$ alkyl halides, such as benzyl chloride and phenethyl bromide. Such salts permit the preparation of both water-soluble and oil-soluble compounds.

Acid and base addition salts may be prepared by contacting the free base form with a sufficient amount of a desired acid or base to produce the salt in a manner known in the art. The free base may be regenerated by contacting the salt form with a base or acid (depending on the nature of the salt) and isolating the free base. The free base forms differ from their respective salt forms somewhat in certain physical properties such as solubility in polar solvents, but otherwise the salts are equivalent to their respective free base forms for purposes described herein.

Multiple salts forms are also considered to be pharmaceutically-acceptable salts. Common, non-limiting examples of multiple salt forms include: bitartrate, diacetate, difumarate, dimeglumine, diphosphate, disodium, and trihydrochloride.

As such, "pharmaceutically acceptable salt" as used herein is intended to mean an active ingredient comprising a salt form of a cyclic adenosine monophosphate. The salt form preferably confers to the cyclic adenosine monophosphate improved and/or desirable pharmacokinetic/pharmodynamic properties.

A cyclic adenosine monophosphate may be incorporated into an adhesion bather by incorporation, adsorption or absorption into or onto a physical adhesion barrier, such as those bathers described herein. A cyclic adenosine monophosphate may be co-administered with other anti-adhesive drugs, for example with adenosine, or with other cyclic adenosine monophosphates, optionally in the same solution or dosage form. A cyclic adenosine monophosphate may be co-administered with other active agents, such as antibiotic drugs, anti-inflammatory drugs, anti-coagulants or fibrolytic agents, optionally in the same solution or dosage form. In one embodiment, a cyclic adenosine monophosphate is formulated into a slow-dissolving or timed release solid of gel for intraperitoneal implantation, by which the cyclic adenosine monophosphate may be released according to a useful release profile over time, for example, over a one week, month, etc. time period (see, generally, Troy, D B, Editor, Remington: The Science and Practice of Pharmacy, $21^{st}$ Ed., Lippincott Williams & Wilkins (2005), pp. 946-53 for descriptions of various timed-release (rate-controlled) drug delivery systems).

Any relevant end-point can be used to determine an amount of a cyclic adenosine monophosphate effective to prevent or mitigate adhesion formation in a subject. The amounts effective to prevent or mitigate adhesion formation in a subject in humans or other animals can be tested in animals, for example as described herein. Effective doses can be determined by reference to a therapeutic window between a minimum and maximum dose. The minimum dose is a dosage below which the cyclic adenosine monophosphate is not effective in preventing or mitigating adhesion formation. The maximum dosage is a dosage above which the drug causes undesirable and/or unacceptable side-effects, including death or other side-effects. The maximum dosage also may be limited by the maximum solubility of the active agent in the drug product. By "effective," it is meant that adhesion formation is prevented or mitigated (reduced) to a clinically or statistically-relevant degree acceptable in the medical, pharmaceutical and/or veterinary arts.

The amount of a cyclic adenosine monophosphate useful in preventing or mitigating adhesion formation in a subject will vary, depending on the compound used, and delivery method, among other factors. In one embodiment, a solution of approximately 75 mM 2',3'-cAMP is administered intraperitoneally (ip) in a formulation that is suitable for ip administration. In another embodiment, a solution comprising, without limitation, from 1 mM to 250 mM, from 10 mM to 150 mM or from 50 mM to 100 mM, from 70 mM to 80 mM, or increments within any of the stated ranges, of a cyclic adenosine monophosphate is administered to a subject. Typically from 1 mL to 1 L of the solution is administered to the subject over a given time period, though more or less may be administered over any given time period. Therefore, according to one non-limiting embodiment, from 1 μMoles (micromoles) to 250 mM (millimoles) is administered to the subject, typically in a given time period, such as hourly or daily, as is effective. The quantity of the solution comprising a cyclic adenosine monophosphate that is administered to a subject in order to prevent or mitigate adhesion formation depends on the concentration of the active agent in the solution, the size of the subject (a larger subject might better physically tolerate larger amounts of a solution), as well as the maximum tolerable dose and the minimum effective dose, all of which can readily be identified by those of ordinary skill in the art. For dosage forms other than intraperitoneal, such as intravenous, oral, suppository, implantation, etc., optimal doses and formulations will need to be determined experimentally, though such experimentation is well within the everyday abilities of those of ordinary skill in the art. In one embodiment, irrespective of delivery route, the dosage form produces intraperitoneal concentration of the cyclic adenosine monophosphate in a range between from 1 mM to 250 mM, from 10 mM to 150 mM or from 50 mM to 100 mM, from 70 mM to 80 mM, or increments within any of the stated ranges. In another non-limiting embodiment, the drug product is administered intraperitoneally using a pump, such as a peristaltic pump, through a patient's abdominal wall.

The cyclic adenosine monophosphate(s) may be compounded or otherwise manufactured into a suitable composition for use, such as a pharmaceutical dosage form or drug product in which the compound is an active ingredient. Compositions may comprise a pharmaceutically acceptable carrier, or excipient. An excipient is an inactive substance used as a carrier for the active ingredients of a medication. Although "inactive," excipients may facilitate and aid in increasing the delivery or bioavailability of an active ingredient in a drug product. Non-limiting examples of useful excipients include: antiadherents, binders, rheology modifiers, coatings, disintegrants, emulsifiers, oils, buffers, salts, acids, bases, fillers, diluents, solvents, flavors, colorants, glidants, lubricants, preservatives, antioxidants, sorbents, vitamins, sweeteners, etc., as are available in the pharmaceutical/compounding arts (see, Troy, D B, Editor, Remington: The Science and Practice of Pharmacy, 21$^{st}$ Ed., Lippincott Williams & Wilkins (2005) for detailed descriptions of various dosage forms, methods of manufacture of such dosage forms and routes of administration of such dosage forms). Excipients may include compounds or compositions that enhance the solubility of the compound. In one preferred embodiment, the dosage form is a solution for ip administration.

Useful dosage forms include: intravenous, intramuscular, or intraperitoneal solutions, oral tablets or liquids, implants (for example intraperitoneal implants), topical ointments or creams and transdermal devices (e.g., patches). In one embodiment, the compound is a sterile solution comprising the active ingredient (drug, or compound), and a solvent, such as water, saline, lactated Ringer's solution, or phosphate-buffered saline (PBS), and optionally comprising glucose. Additional excipients, such as, without limitation, polyethylene glycol, emulsifiers, salts and buffers may be included in the solution. By "dose" it is meant an amount of a drug product administered to a subject at any given time, whether or not a single or unit dose, such as a single tablet, capsule, spray, puff, auto-injection, etc., or multiple unit doses are administered. An oral dosage form is a drug product that is suitable for administration orally, such as a tablet, capsule, caplet, syrup etc.

The present invention will now be further illustrated by, but is by no means limited to, the following example. It will be apparent to those skilled in the art that many modifications, both to materials and methods may be practical without departing from the purpose and interest of this invention.

Example 1

This protocol examined the effects of several treatments on post-surgical adhesion formation. Six-week-old C57Bl mice were fasted overnight and then anesthetized the following day with an intraperitoneal injection of pentobarbital (50 mg/kg). The surgical procedures were conducted under aseptic conditions. The abdomen was shaved to remove hair, and the incision site was cleaned with betadine solution. Surgery was performed under a laminar flow hood using instruments sterilized in a glass bead sterilizer. The abdomen was opened via a midline incision of approximately 10 mm. The cecum was exposed and placed on sterile gauze. A sterile pediatric electric toothbrush was used to damage both sides of the cecum (brushing for 1.5 minutes on each side of the cecum for a total of 3 minutes). In addition to the mechanically-induced tissue injury, 20 microliters of 95% ethanol was applied to the cecum to cause further chemically-induced tissue injury. After 30 seconds, the ethanol was washed from the cecum surface with 1-ml of test solution. Next, the cecum was returned to the peritoneal cavity and placed in its natural position. Then 1-ml of test solution was placed in the peritoneal cavity, and the abdominal incision was repaired by suturing. Mice were treated with antibiotics at this time to prevent infection [penicillin benzathine salt (0.05 ml of a 20 mg/ml preparation injected into the thigh) and enrofloxacin (0.15 ml of a 1.15 mg/ml preparation injected subcutaneously)]. The animals were placed under a warming lamp and observed until they regained consciousness. After regaining consciousness, the mice were placed back in the housing cage.

Ten days later, the animals were again anesthetized with pentobarbital, and the abdomen was surgically opened to provide a clear view of the intestines. The severity of adhesion formation was assessed on a semi-quantitative scale from 1 to 5, taking into account the extent of adhesion formation (with 1 being the least amount of adhesion formation and 5 being the most amount of adhesion formation). Adhesions were identified visually and by noting the difficulty of separating adjacent surfaces. Adhesion scores were assigned by an individual blinded to (that is unaware of) the test solutions used to treat the animals. The scoring was based on the extent of adhesion of the cecum to itself and to adjacent tissues or organs. A score of 1 was assigned to animals when there was only minimal (approximately >10 to <20%) adhesion of the cecum to itself (that is within the cecum core) with no adhesion of the cecum to other adjacent structures (abdominal wall, liver or intestines). A score of 2 was assigned when there was mild (approximately >20 to <30%) adhesion of the cecum to itself or when there was minimal (approximately >10 to <20%) adhesion of the cecum to itself but in addition minimal adhesion of the cecum to adjacent structures. A score of 3 was assigned to animals when the adhesion of the cecum to itself was moderate (approximately >30 to <50%), in the absence or presence of minimal adhesion of the cecum to adjacent structures. A score of 4 was assigned to animals when the adhesion of the cecum to itself was severe (approximately >60 to <80%) or when there was moderate adhesion to adjacent structures or both. A score of 5 was assigned to animals when adhesion of the cecum to itself was so extensive that it existed as one entity (complete adhesion within itself) or when there was severe adhesion of the cecum to itself but in addition severe adhesion of the cecum to adjacent structures.

In this example, there were six groups that were treated with test solutions containing chemical agents of interest. In addition, there was a seventh group (the control group) in which the test solution was only the vehicle in which the chemical agents of interest were dissolved. The vehicle for all six test solutions was 0.9% saline, so the seventh group (control group) received only 0.9% saline as the test solution. The test solution, the number of animals (n-value) and the associated adhesion scores (mean±standard error of mean) were:

Saline (control group; n=18): 4.72±0.11.
Adenosine (23 millimoles/L; n=12): 3.08±0.15
5'-adenosine monophosphate (75 millimoles/L; n=11): 3.82±0.18
3'-adenosine monophosphate (75 millimoles/L; n=12): 4.00±0.17
2'-adenosine monophosphate (75 millimoles/L; n=12): 4.08±0.15
3',5'-cyclic adenosine monophosphate (75 millimoles/L; n=19): 2.89±0.11
2',3'-cyclic adenosine monophosphate (75 millimoles/L; n=20): 2.5±0.11.

As can be seen above, the apparent order of efficacy for attenuating adhesion formation was: 2',3'-cyclic adenosine monophosphate which was better than 3',5'-cyclic adenosine monophosphate which was approximately the same as adenosine which was better than 5'-adenosine monophoshate which was approximately the same as 3'-adenosine monophosphate which was approximately the same as 2'-adenosine monophosphate. The seven groups were compared using a 1-factor analysis of variance with independent groups. The overall p-value for differences among the groups was p<0.000001. Thus, there was less than one chance in a million that the groups were equivalent. Post-hoc analysis with a protected Fisher's Least Significant Difference test was used to identify which groups were different. All treatment groups had adhesions scores that were significantly (p<0.05) less than (better than) the saline control group. However, the adhesion scores for 5'-adenosine monophoshate, 3'-adenosine monophoshate and 2'-adenosine monophoshate were nominally similar, not significantly different from each other and only slightly less than (better than) that for the saline control group. This indicates that although these three adenosine monophosphates decrease adhesion formation, the effect is indeed very small. The adhesion scores for adenosine and 3',5'-cyclic adenosine monophosphate were nominally similar, not significantly different from each other, less than (better than) 5'-adenosine monophosphate ($p<0.05$), 3'-adenosine monophosphate ($p<0.05$) and 2'-adenosine monophosphate ($p<0.05$), but more than (not as good as) 2',3'-cyclic adenosine monophosphate ($p<0.05$). Finally, the analysis showed that 2',3'-cyclic adenosine monophosphate significantly ($p<0.05$) improved adhesion scores better than all other treatments.

TABLE 1 adhesion scores for all mice
Treatment Group

| Saline | Adenosine | 5'-AMP | 3'-AMP | 2'-AMP | 3',5-cAMP | 2',3'-cAMP |
|---|---|---|---|---|---|---|
| 4 | 4 | 4 | 5 | 4 | 3 | 2 |
| 5 | 3 | 4 | 5 | 4 | 3 | 2 |
| 5 | 3 | 3 | 4 | 5 | 2 | 2 |
| 5 | 3 | 4 | 4 | 4 | 3 | 3 |
| 4 | 3 | 4 | 4 | 4 | 3 | 2 |
| 4 | 3 | 4 | 4 | 3 | 3 | 2 |
| 5 | 3 | 3 | 3 | 4 | 2 | 3 |
| 4 | 4 | 3 | 4 | 4 | 3 | 2 |
| 5 | 3 | 4 | 4 | 5 | 3 | 3 |
| 4 | 3 | 5 | 3 | 4 | 3 | 3 |
| 5 | 3 | 4 | 4 | 4 | 3 | 3 |
| 5 | 2 |  | 4 | 4 | 3 | 3 |
| 5 |  |  |  |  | 3 | 2 |
| 5 |  |  |  |  | 3 | 3 |
| 5 |  |  |  |  | 2 | 3 |
| 5 |  |  |  |  |  | 2 |
| 5 |  |  |  |  |  | 3 |
| 5 |  |  |  |  |  | 2 |
|  |  |  |  |  |  | 3 |
|  |  |  |  |  |  | 2 |

5'-AMP, 5'-adenosine monophosphate; 3'-AMP, 3'-adenosine monophosphate; 2'-AMP, 2'-adenosine monophosphate; 3',5'-cAMP, 3',5'-cyclic adenosine monophosphate; 2',3'-cAMP, 2',3'-cyclic adenosine monophosphate.

Although not formally scored, it was also observed that the structures within the abdominal cavity in the group treated with 2',3'-cyclic adenosine monophosphate and 3',5'-cyclic adenosine monophosphate appeared less inflamed and generally healthier than the other groups.

Example 2

The results of EXAMPLE 1 show that as predicted, at a concentration of 75 millimoles/L, both 2'-adenosine monophosphate and 3'-adenosine monophosphate were nearly inactive; but surprisingly 5'-adenosine monophosphate, which is a direct prodrug of adenosine because it requires only a single metabolic step to be converted to adenosine, also was nearly inactive. Also surprising was the finding that 3',5'-cyclic adenosine monophosphate (75 millimoles/L) was as efficacious as adenosine and more efficacious than 5'-adenosine monophosphate with respect to inhibiting the formation of post-surgical abdominal adhesions. Most surprising was the result with 2',3'-cyclic adenosine monophosphate, a compound that, unlike 3',5'-cyclic adenosine monophosphate, is not known to be metabolized to adenosine. Based on these results, we proposed the hypothesis that 2',3'-cyclic adenosine monophosphate and 3',5'-cyclic adenosine monophosphate inhibit post-surgical abdominal adhesions via a mechanism independent of adenosine formation. To test this hypothesis, we conducted another experiment as described for EXAMPLE 1, with the exception that the test solutions were either:

1,3-dipropyl-8-(p-sulfophenyl)xanthine (1 mM)+Saline
1,3-dipropyl-8-(p-sulfophenyl)xanthine (1 mM)+adenosine (23 mM)
1,3-dipropyl-8-(p-sulfophenyl)xanthine (1 mM)+3',5'-cyclic adenosine monophosphate (75 mM)
1,3-dipropyl-8-(p-sulfophenyl)xanthine (1 mM)+2',3'-cyclic adenosine monophosphate (75 mM)

1,3-dipropyl-8-(p-sulfophenyl)xanthine is a water soluble adenosine receptor antagonist that at 1 mM blocks all four P1 adenosine receptor subtypes ($A_1$, $A_{2A}$, $A_{2B}$ and $A_3$, see, e.g., Table 19-1 of Chapter 19 by J. W. Daly and K. A. Jacobson in ADENOSINE AND ADENINE NUCLEOTIDES: From Molecular Biology to Integrative Physiology, edited by L. Belardinelli and A. Pelleg, Kluwer Academic Publishers, Boston, 1995). Therefore, if 2',3'-cyclic adenosine monophosphate and 3',5'-cyclic adenosine monophosphate attenuate post-surgical adhesion formation via conversion to adenosine, these compounds should be ineffective in the presence of 1,3-dipropyl-8-(p-sulfophenyl)xanthine. As a control to validate that 1 mM of 1,3-dipropyl-8-(p-sulfophenyl)xanthine indeed inhibits the anti-adhesion actions of adenosine, a group treated with both 1,3-dipropyl-8-(p-sulfophenyl)xanthine and adenosine was included. Also, to validate that 1,3-dipropyl-8-(p-sulfophenyl)xanthine per se has little or no effect on adhesion formation, a group treated only with 1,3-dipropyl-8-(p-sulfophenyl)xanthine was also included. The results are shown below in Table 2.

TABLE 2

All Groups Treated with 1,3-Dipropyl-8-(p-Sulfophenyl)Xanthine

| Saline | Adenosine | 3',5'-cAMP | 2',3'-cAMP |
|---|---|---|---|
| 5 | 4 | 3 | 3 |
| 5 | 4 | 3 | 3 |
| 5 | 4 | 3 | 2 |
| 4 | 5 | 4 | 3 |

3',5'-cAMP, 3',5'-cyclic adenosine monophosphate; 2',3'-cAMP, 2',3'-cyclic adenosine monophosphate The test solution (all treated with 1,3-dipropyl-8-(p-sulfophenyl)xanthine), the number of animals (n-value) and the associated adhesion scores (mean±standard error of mean) were:

Saline (control group; n=4): 4.75±0.22
Adenosine (23 millimoles/L; n=4): 4.25±0.22
3',5'-cylic adenosine monophosphate (75 millimoles/L; n=4): 3.25±0.22 2',3-cyclic adenosine monophosphate (75 millimoles/L; n=4): 2.75±0.22

The four groups were compared using a 1-factor analysis of variance with independent groups. The overall p-value for differences among the groups was $p<0.0004$. Post-hoc analysis with a protected Fisher's Least Significant Difference test was used to identify which groups were different. In this regard, both the 3',5'-cylic adenosine monophosphate and the 2',3'-cylic adenosine monophosphate groups significantly ($p<0.05$) attenuated the adhesion score compared to either the saline group or the adenosine group. In contrast, adenosine did not significantly reduce the adhesion score compared with the saline group. These data indicate that 1,3-dipropyl-8-(p-sulfophenyl)xanthine blocks the anti-adhesion effects of adenosine, but not the anti-adhesion effects of either 3',5'-cylic adenosine monophosphate or 2',3'-cylic adenosine monophosphate. These data thus support the concept that both 3',5'-cylic adenosine monophosphate and 2',3'-cylic adenosine monophosphate exert anti-adhesion activity independent of adenosine formation.

Having described this invention above, it will be understood to those of ordinary skill in the art that the same can be performed within a wide and equivalent range of conditions, formulations and other parameters without affecting the scope of the invention or any embodiment thereof. Any document incorporated herein by reference is only done so to the extent of its technical disclosure and to the extent it is consistent with the present application and the disclosure provided herein.

I claim:

1. A method of reducing the formation of adhesions in a mammalian subject in need thereof, comprising administering to the subject 2',3'-cyclic adenosine monophosphate or a pharmaceutically acceptable salt thereof able to reduce the formation of adhesions in a subject as compared to adenosine monophosphate, wherein the 2',3'-cyclic adenosine monophosphate or pharmaceutically acceptable salt thereof is administered to the subject in an amount effective to reduce adhesions in the subject.

2. The method of claim 1, in which the compound is 2',3'-cyclic adenosine monophosphate.

3. The method of claim 1, wherein said mammalian subject is a human.

4. The method of claim 1, wherein the adhesion formation is due to surgery.

5. The method of claim 4, wherein the surgery is abdominal surgery.

6. The method of claim 4, wherein the surgery is pelvic surgery.

7. The method of claim 1, in which a solution of from 1 µMoles to 250 mMoles of the 2',3'-cyclic adenosine monophosphate or pharmaceutically acceptable salt thereof is administered to the subject.

8. A method of reducing inflammation or tissue damage in a mammalian subject in need thereof after abdominal or pelvic surgery, comprising administering to the subject 2',3'-cyclic adenosine monophosphate or a pharmaceutically acceptable salt thereof able to reduce inflammation or tissue damage in a subject as compared to adenosine monophosphate, wherein the 2',3'-cyclic adenosine monophosphate or pharmaceutically acceptable salt thereof is administered to the subject in an amount effective to reduce inflammation or tissue damage.

9. The method of claim 8, in which the compound is 2',3'-cyclic adenosine monophosphate.

10. The method of claim 8, wherein said mammalian subject is a human.

11. The method of claim 8, in which a solution of from 1 µMoles to 250 mMoles of the 2',3'-cyclic adenosine monophosphate or pharmaceutically acceptable salt thereof is administered to the subject.

* * * * *